United States Patent
Seppälä et al.

(10) Patent No.: US 12,263,025 B2
(45) Date of Patent: *Apr. 1, 2025

(54) CT IMAGING APPARATUS

(71) Applicant: PLANMECA OY, Helsinki (FI)

(72) Inventors: Lauri Seppälä, Helsinki (FI); Timo Müller, Helsinki (FI); Tommi Syrjälä, Helsinki (FI)

(73) Assignee: Planmeca OY, Helsinki (FI)

( * ) Notice: Subject to any disclaimer, the term of this patent is extended or adjusted under 35 U.S.C. 154(b) by 0 days.

This patent is subject to a terminal disclaimer.

(21) Appl. No.: 18/203,788

(22) Filed: May 31, 2023

(65) Prior Publication Data

US 2023/0301603 A1   Sep. 28, 2023

Related U.S. Application Data

(63) Continuation of application No. 16/714,337, filed on Dec. 13, 2019, now Pat. No. 11,684,319.

(30) Foreign Application Priority Data

Jun. 3, 2019   (FI) .................................... 20190042
Jul. 5, 2019   (FI) .................................... 20190054

(51) Int. Cl.
*A61B 6/03*   (2006.01)
*A61B 6/00*   (2006.01)
(Continued)

(52) U.S. Cl.
CPC .............. *A61B 6/032* (2013.01); *A61B 6/035* (2013.01); *A61B 6/0407* (2013.01); *A61B 6/08* (2013.01); *A61B 6/40* (2013.01); *A61B 6/4429* (2013.01); *A61B 6/4435* (2013.01); *A61B 6/4452* (2013.01); *A61B 6/4476* (2013.01);
(Continued)

(58) Field of Classification Search
None
See application file for complete search history.

(56) References Cited

U.S. PATENT DOCUMENTS

4,385,397 A * 5/1983 Verro .................... A61B 6/4447
                                                 378/20
5,206,512 A * 4/1993 Iwao ..................... G01T 1/1648
                                                 250/363.04
(Continued)

*Primary Examiner* — Marcus H Taningco
(74) *Attorney, Agent, or Firm* — Lippes Mathias LLP (57) ABSTRACT

A dental or medical CT imaging apparatus including a first longitudinally extending frame part. A support construction extends substantially perpendicularly from the longitudinally extending frame part. An X-ray source and an image detector which together form an X-ray imaging assembly are mounted to the support construction. A first driving mechanism is provided to move the X-ray imaging assembly about a virtual or physical rotation axis. A control system having at least one operation mode that simultaneously controls the first driving mechanism and the X-ray imaging assembly is provided. The support construction includes at least one guiding mechanism configured to enable laterally moving at least one of the X-ray source and the image detector in relation to the support construction. A range of the lateral movement of at least one of the X-ray source and the image detector includes a base position and a first and a second extreme position.

20 Claims, 8 Drawing Sheets

(51) Int. Cl.
  *A61B 6/04*     (2006.01)
  *A61B 6/08*     (2006.01)
  *A61B 6/40*     (2024.01)
  *A61B 6/51*     (2024.01)
  *A61B 6/58*     (2024.01)
  *A61B 5/00*         (2006.01)

(52) U.S. Cl.
  CPC ............ *A61B 6/51* (2024.01); *A61B 6/54* (2013.01); *A61B 6/587* (2013.01); *A61B 5/0088* (2013.01)

(56) References Cited

U.S. PATENT DOCUMENTS

| | | | | |
|---|---|---|---|---|
| 5,519,222 | A * | 5/1996 | Besett | G01T 1/1648 250/363.04 |
| 5,717,212 | A * | 2/1998 | Fulton | G01T 1/1648 250/363.05 |
| 7,147,373 | B2 * | 12/2006 | Cho | A61N 5/1049 378/207 |
| 11,684,319 | B2 * | 6/2023 | Seppala | A61B 6/4452 378/4 |
| 2010/0290584 | A1 * | 11/2010 | Vesel | A61B 6/4283 378/210 |
| 2011/0129061 | A1 * | 6/2011 | Janbakhsh | A61B 6/032 250/363.05 |
| 2014/0139215 | A1 * | 5/2014 | Gregerson | A61B 6/4476 324/309 |
| 2015/0342543 | A1 * | 12/2015 | Khen | G06T 11/005 250/362 |
| 2017/0215826 | A1 * | 8/2017 | Johnson | H02G 11/006 |

* cited by examiner

CT IMAGING APPARATUS

BACKGROUND

The present disclosure relates to computed tomography imaging apparatus. Structures of an apparatus are applicable for use in the context of dental and medical cone beam computed tomography (CBCT) imaging apparatus.

Computed tomography (CT) is a kind of X-ray imaging in which a volume to be imaged is irradiated from different directions and, from the image information thus acquired, a desired two- or three-dimensional image can be reconstructed.

Traditional CT apparatus are large and massive, and they are typically mounted on a floor. A patient is positioned for imaging within an examination opening of the apparatus, typically on a horizontally extending and laterally movable examination platform.

Since development of cone beam computed tomography (CBCr) technology in which, for one, slower rotational speeds of the imaging means are used, apparatus of less weight than that of the more traditional CT apparatus have been developed. Among the CBCr apparatus, there are also e.g. ones which are not floor mounted but are constructed to be mobile. Also, constructions comprising a vertically extending frame and a horizontally extending support for the imaging means have been designed.

Considering medical X-ray imaging apparatus in general, those comprising a patient support construction are typically designed in view of imaging either a standing patient, a sitting patient or a lying patient.

Some of the CT apparatus designed in recent times are multipurpose apparatus supporting more than one imaging modality which tends to increase complexity of the apparatus, e.g. as a consequence of a new kind of freedom of movement having been arranged to one or more components of the apparatus. Also, the weight of the apparatus may then increase, while some modifications may e.g. generate new challenges relating to getting a patient positioned for an exposure.

As an example, in U.S. Pat. No. 7,945,012, the disclosure of which is herein incorporated by reference, a computed tomography method is disclosed which includes emitting radiation from a location which is transversely displaced from a center of a transverse field of view, but no detailed structural embodiments by which to realize the movements needed to realize the imaging modes are provided.

BRIEF DESCRIPTION

The present disclosure is directed to a CT apparatus, especially a CBCr apparatus, including features related to mutual positioning of the apparatus and a patient for an exposure. In one embodiment, the apparatus may perform imaging exposure according to more than one imaging mode.

More particularly, the CT apparatus of the present disclosure is directed to a dental or medical CT imaging apparatus including a first longitudinally extending frame part. A support construction extends substantially perpendicularly from the longitudinally extending frame part. An X-ray source and an image detector which together form an X-ray imaging assembly are mounted to the support construction. A first driving mechanism is provided to move the X-ray imaging assembly about a virtual or physical rotation axis. A control system having at least one operation mode that simultaneously controls the first driving mechanism and the X-ray imaging assembly is provided. The support construction includes at least one guiding mechanism configured to enable laterally moving at least one of the X-ray source and the image detector in relation to the support construction. A range of the lateral movement of at least one of the X-ray source and the image detector includes a base position and a first and a second extreme position.

BRIEF DESCRIPTION OF THE FIGURES

The invention is now described in more detail in reference to some of its preferable embodiments and the attached drawings, of which.

DETAILED DESCRIPTION

A more complete understanding of the components, processes and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise. As used herein, the terms about, generally and substantially are intended to encompass structural or numerical modifications which do not significantly affect the purpose of the element or number modified by such term. For example, the term substantially may include a range of variance such as 25%, or 10%, or 0% from the stated relationship.

As used in the specification and in the claims, the term "comprising" may include the embodiments "consisting of" and "consisting essentially of.," The terms "comprise(s)," "include(s)," "having," "has," "can," "contain(s)," and variants thereof, as used herein, are intended to be open-ended transitional phrases, terms, or words that require the presence of the named elements/steps and permit the presence of other elements/steps.

Figure 1:
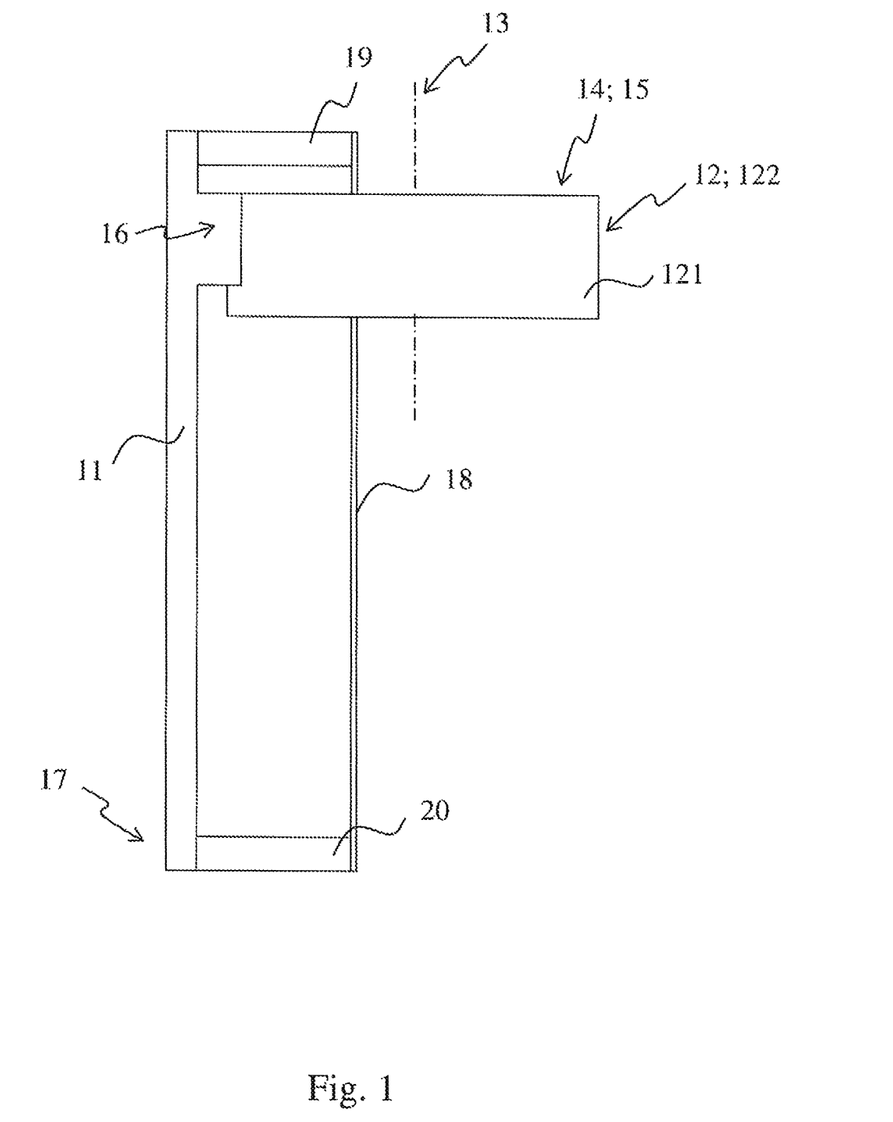
FIG. 1 is a schematic side view of an imaging apparatus of the present disclosure.

FIG. 1 displays a longitudinally extending frame part 11 extending in a first direction and having a first end and a second end. From this longitudinally extending frame part 11, or "an elongated frame part 11", extends in a second direction a support construction 12 which supports an X-ray source 14 and an image detector 15, the second direction is substantially orthogonal to the first direction. The X-ray source 14 and the image detector 15, which components together form an X-ray imaging assembly, may be mounted to the support construction 12 essentially opposite to each other yet in embodiments of the disclosure, their position is also adjustable. Of course, the person of ordinary skill in the art will appreciate that the X-ray imaging assembly is composed of the X-ray source, image detector and such other components as typically employed in the field of computed tomography.

While apparatus like the ones discussed above often include a patient support, FIG. 1 shows a specific patient support 18 structure mechanically connected to the elongated frame part 11. This patient support 18, applicable for use in various embodiments of the disclosure to be discussed in some more detail further below, comprises a surface which extends substantially in parallel with the elongated frame part 11. And while such patient support 18 is optional concerning some embodiments, in the embodiment of FIG. 1 the patient support 18 is essentially of the same length as the elongated frame part 11.

According to one aspect of the disclosure, for example, the length of the elongated frame part 11 is of the order of 240 cm.

According one aspect of the disclosure, for example, the length of the elongated frame part 11 is between 220 cm and 260 cm.

According one aspect of the disclosure, for example, the length of the patient support 18 is 80-90 t of the length of elongated frame part 11.

According to one aspect of the disclosure, for example, the patient support 18 has a longer dimension in a first direction and a shorter dimension in a second direction orthogonal to the first direction.

According to one aspect of the disclosure, for example, the patient support 18 is at least in the first direction for at least its prevailing part radiolucent.

According to one aspect of the disclosure, for example, the radiolucent part of the patient support 18 is of essentially the same length as the elongated frame part 11.

According to one aspect of the disclosure, for example, the patient support 18 comprises at least at either of its ends in the first direction a section which is not radiolucent.

According one aspect of the disclosure, for example, the length of the radiolucent part of the patient support 18 in the first direction is 80-90% of the length of the elongated frame part 11.

In general, the support construction 12 for the X-ray imaging assembly components 14, 15 may comprise a housing 121 which covers a ring-shaped rotatable gantry 122, to which the X-ray imaging assembly 14, 15 are mounted. In one embodiment, the housing 121 may extend to cover the X-ray source 14 and the image detector 15, in another the gantry housing 121 may cover the construction by which the X-ray source 14 and the image detector 15 are connected to the gantry 122 while not the X-ray source 14 and the image detector 15 themselves.

The X-ray imaging assembly 14, 15 may be arranged to be rotatable about a rotation axis 13. In the construction shown in FIG. 1, this rotation axis 13 coincides or can be made to coincide with the central axis of the support construction 12 for the X-ray imaging assembly 14, 15, of the housing 121 and of the rotatable gantry 122 as discussed above. Thus, according to one aspect of the disclosure, for example, the apparatus comprises a driving mechanism 16 arranged to drive the X-ray imaging assembly 14, 15 about a rotation axis 13. The rotation axis 13 may be a physical axis, or a virtual rotation axis as in the case of FIG. 1.

According to one aspect of the disclosure, for example, the rotation axis 13, or the center of rotation of the X-ray imaging assembly 14, 15 when being driven along a curved path and thus defining a location of the virtual rotation axis 13, coincides with the central axis 13 of the gantry 122.

According to one aspect of the disclosure, the rotation axis 13 is an instantaneous (virtual) rotation axis and the location of the instantaneous rotation axis in relation to the central axis of the support construction 12 for the X-ray imaging assembly 14, 15, of the housing 121 and/or of the rotatable gantry 122 as discussed above can be arranged to be changed.

According to one aspect of the disclosure, at least either of the components the ray source 14 and the image detector 15 is arranged to be laterally movable from a location exactly opposite to the other component.

According to one aspect of the disclosure, the support construction 12 for the X-ray imaging assembly 14, 15 comprises a gantry 122 having a central axis and the structures of apparatus allow for at least either of: laterally moving the X-ray source 14 between positions at which a central ray it generates coincides the central axis of the gantry 122 and a position at which the central ray it generates does not coincide with the central axis of the gantry 122; laterally moving the image detector 15 between positions at which a vector which is normal to the detector surface at the center of the image detector 15 coincides with the central axis of the gantry 122 and a position at which the vector which is normal to the detector surface at the center of the image detector 15 does not coincide with the central axis of the gantry 122. The lateral moving of the X-ray imaging assembly 14, 15 may include moving the X-ray imaging assembly 14, 15 to a position at which they face each other while the central ray the X-ray source 14 generates does not coincide the central axis of the gantry 122 and the vector which is normal to the detector surface at the center of the image detector 15 does not coincide with the central axis of the gantry 122.

Rotation of the rotatable gantry 122 may be performed by any conventional mechanism known to those skilled in art. In one exemplary embodiment, a driving belt driven by at least one pulley is arranged to extend around a ring-shaped rotatable gantry 122. Such construction can enable implementing rotating the gantry 122 over an angle exceeding 360 degrees.

According to another aspect of the disclosure, another driving mechanism 17 is arranged to the apparatus to enable moving the support construction 12 for the X-ray imaging assembly 14, 15 back and forth in a direction which is substantially parallel with the direction in which the elongated frame part 11 extends. According to one embodiment, driving mechanism 17 is arranged to move the support construction 12 along or alongside the elongated frame part 11.

The driving mechanism 17 to drive the support construction 12 in a direction which is substantially parallel with the direction in which the elongated frame part 11 extends can comprise a motor arranged to the support construction 12 for the X-ray imaging apparatus 14, 15 itself.

Regardless of the details of the construction of the driving mechanism 17 to drive the support construction 12 along or alongside the elongated frame part 11, in one embodiment the construction of the apparatus allows for driving the support construction 12 essentially the whole length between the first and second ends of the elongated frame part 11.

While details of the driving mechanism 17 for moving the support construction 12 for the X-ray imaging assembly 14, 15 back and forth in a direction which is substantially parallel with the direction in which the elongated frame part 11 extends may vary, one example of such mechanism is disclosed in patent application FI 20190054, which is herein incorporated by reference.

The apparatus of this disclosure can be described as a dental or medical CT imaging apparatus which comprises:
- a first longitudinally extending frame part 11 comprising a first end and a second end;
- a support construction 12 extending from the longitudinally extending frame part 11 in a second direction essentially at right angles to the first direction;
- an X-ray source 14 and an image detector 15 which together form an X-ray imaging assembly 14, 15 mounted to the support construction 12;
- a first driving mechanism 16 arranged to move the X-ray imaging assembly components 14, 15 about a virtual or physical rotation axis 13.

The apparatus also includes a control system, some implementations of which will be discussed further below. The control system of the apparatus may comprise at least one operation mode to operate the first driving mechanism 16 as defined above and to simultaneously operate the X-ray imaging assembly 14, 15.

Figure 2A:
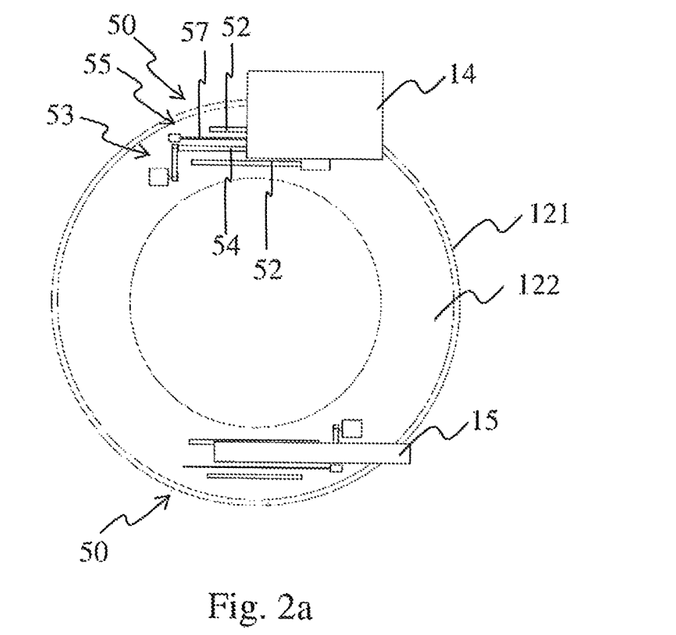
FIGS. 2a-2c display an embodiment including a motorized guiding mechanism arranged in functional connection with the imaging assembly of the apparatus.
Figure 2B:
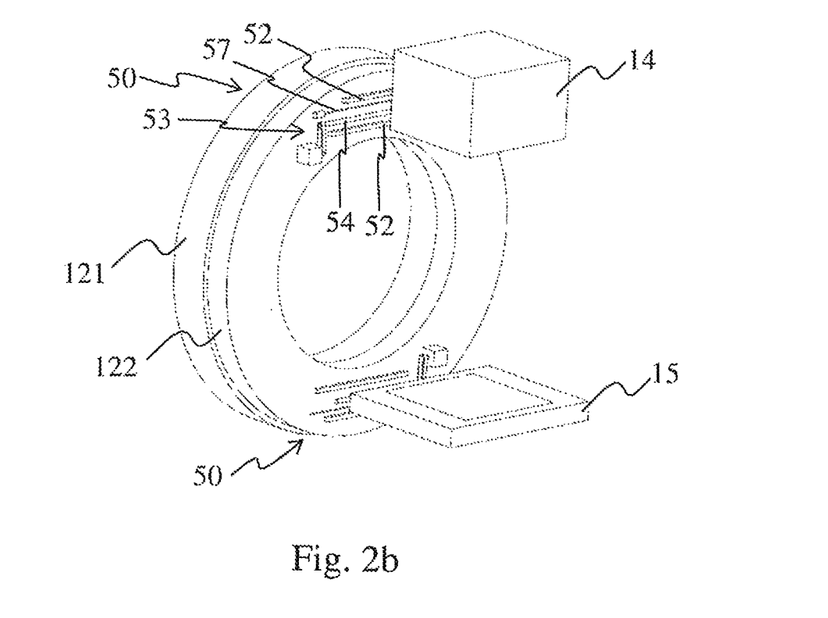
Figure 2C:
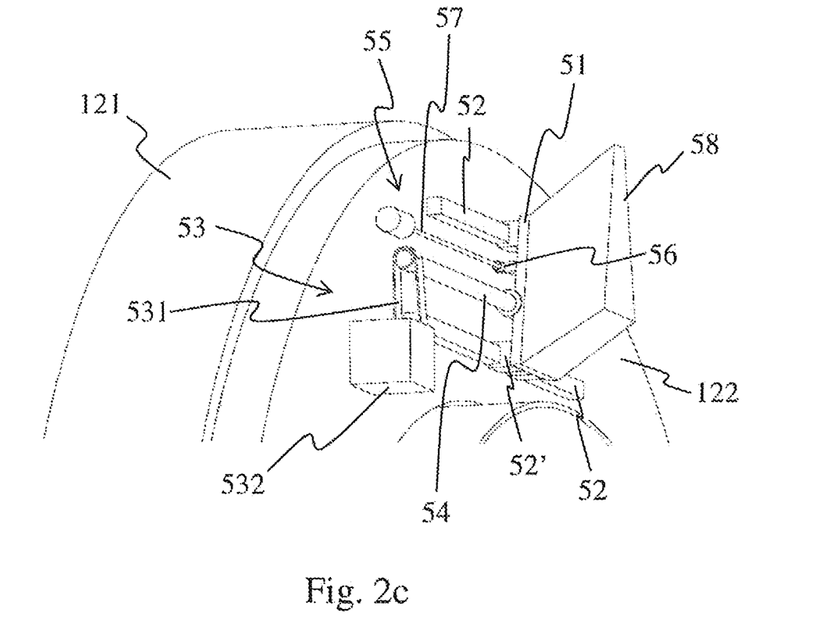

Turning to FIGS. 2a-2c a portion of the housing 121 has been removed to reveal a guiding construction 50 which can be arranged in functional connection with at least one of the X-ray source 14 and the image detector 15. According to one embodiment, the guiding construction 50 is motorized.

While FIGS. 2a-2c show two guiding constructions 50, which are configured to enable laterally moving the X-ray source 14 and the image detector 15 in relation to their support construction 12, or in relation to the gantry 122, according to another embodiment only one of the X-ray source 14 and the image detector 15 includes a guiding construction.

The lateral movement of the X-ray source 14 and/or the image detector 15 in relation to the support construction 12, or the gantry 122, can be implemented to take place on a plane which is orthogonal to the rotation axis 13.

According to one embodiment, for example, the at least one guiding construction 50 as discussed herein is mounted to a ring-shaped gantry 122 arranged to the support construction 12 supporting the X-ray imaging assembly 14, 15.

The range of lateral movement of at least one of the X-ray source 14 and the image detector 15, provided by the guiding construction 50, may comprise a base position and a first and a second extreme position in opposite directions from the base position.

While FIGS. 2a-2c show an embodiment in which structurally identical guiding constructions 50 are arranged for both the X-ray source 14 and the image detector 15, and show the guiding construction 50 in different details, for clarity of the FIGS. while not all the components are not even visible in all of those, not each and every component is presented in each of the FIGS. 2a-2c with a related reference number.

According to one embodiment, the apparatus comprises a guiding construction 50 for at least one of the X-ray source 14 and the image detector 15, the guiding construction 50 comprising a carriage 51 (visible in FIG. 2c) mounted to the X-ray source 14 and/or the image detector 15, to enable lateral moving of at least one of the X-ray source 14 and the image detector 15. A range of the lateral movement of the carriage 51 may include a base position and first and second extreme positions in opposite directions from the base position.

Further, according to one aspect, the at least one guiding construction 50 comprises at least one guiding groove or rail 52 on the side of the support construction 12, or of the gantry 122, and a mating construction 52' on the side of the carriage 51 (again, visible in FIG. 2c).

The at least one guiding construction 50 can comprise a motorized construction 53 in functional connection with the carriage 51, the motorized construction 53 providing the lateral movement of the X-ray source 14 and/or the image detector 15 within the range comprising the first and second extreme positions.

The motorized construction 53 can comprises a driving screw 54 which is aligned parallel with the at least one guiding groove or rail 52 and arranged in functional connection with the carriage 51. According to the embodiment shown in FIGS. 2a-2c, the driving screw 54 is arranged to be rotated via a belt 531 driven by a motor 532. Of course, the present disclosure contemplates other constructions to rotate the driving screw 54.

The guiding construction 50 can include a position sensor arrangement 55 configured to acquire information relating to a position of the X-ray source 14 and/or the image detector 15, within the range of the lateral movement. The position sensor arrangement 55 can be configured to detect a position of the carriage 51 within the range of the lateral movement of the carriage 51.

According to one further aspect, a signal path can be arranged between the at least one guiding construction 50 and the control system of the apparatus. The signal path can comprise a signal path between the position sensor arrangement 55 and the control system of the apparatus.

According to one embodiment, the position sensor arrangement 55 can be an absolute position sensor arrangement 55. The absolute position sensor arrangement 55 can comprise a magnetic component 56 structurally connected to the carriage 51 and movably connected to a rod 57 extending in parallel with the at least one guiding groove or rail 52 and the driving screw 54.

According to one another embodiment, the first longitudinally extending frame part 11 can extend horizontally or is arranged to be moved so as to extend horizontally and the motorized construction 53 of the guiding construction 50 is arranged as self-holding regarding all i) positions of at least either of the X-ray source 14 and the image detector 15 within the range of their lateral movement and ii) rotational positions at which the first driving mechanism 16 is configured to move the X-ray source 14 and the image detector 15 about the rotation axis 13.

Figure 3:
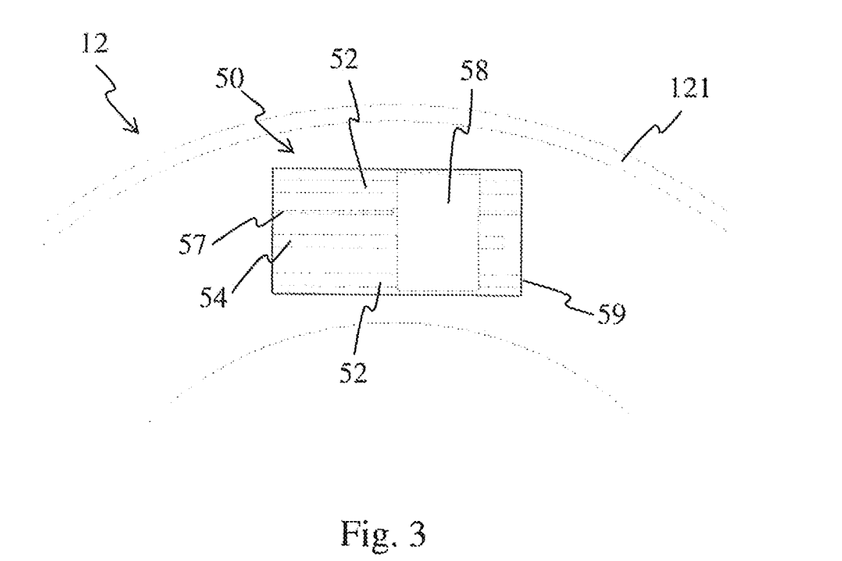
FIG. 3 shows the guiding mechanism of FIGS. 2a-2c as partially covered by a housing of a support construction of the imaging assembly of the apparatus.
Figure 4:
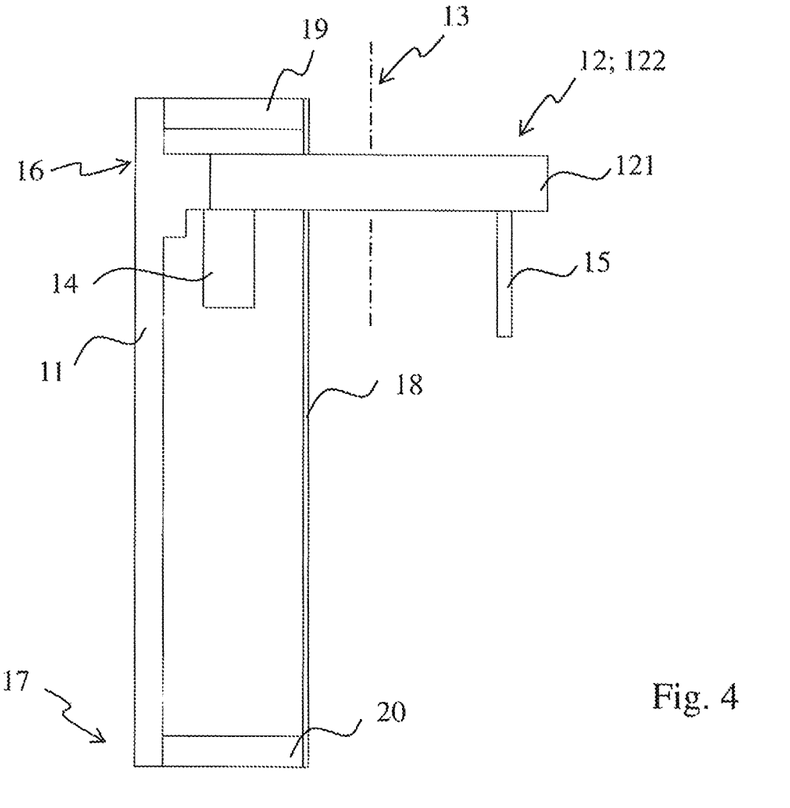
FIG. 4 is a schematic top view showing an embodiment in which the imaging assembly of the apparatus extend outside of the housing of the support construction.

In reference to FIGS. 3 and 4, an embodiment of disclosure shows the support construction 12 for the X-ray imaging assembly components 14, 15 as a ring-shaped gantry housing 121 which houses i) the at least one guiding construction 50 and optionally also ii) the first driving mechanism, whereas the X-ray source 14 and the image detector 15 are positioned or arranged to extend outside the ring-shaped gantry housing 121.

According to one embodiment, the X-ray source 14 and the image detector 15 extend from a same side of the ring-shaped gantry housing 121 and that side of the ring-shaped gantry housing 121 can comprise a closed surface which includes is an opening 59 through which at least one of the X-ray source 14 and the image detector 15 extend. The opening 59 can be dimensioned to allow for the range of lateral movement of the X-ray source 14 and/or the image detector 15 as guided by the at least one guiding construction 50.

As depicted in FIGS. 2c and 3, a mounting bracket 58 can be configured to extend through the opening 59 in the gantry housing 121. Mounting bracket 58 can be fixed to the carriage 51 at one side and support the X-ray source 14 and/or the image detector 15 at the other. As reflected in FIGS. 2c and 3, it is clear that differently dimensioned mounting brackets 58 can be used.

Figure 5:
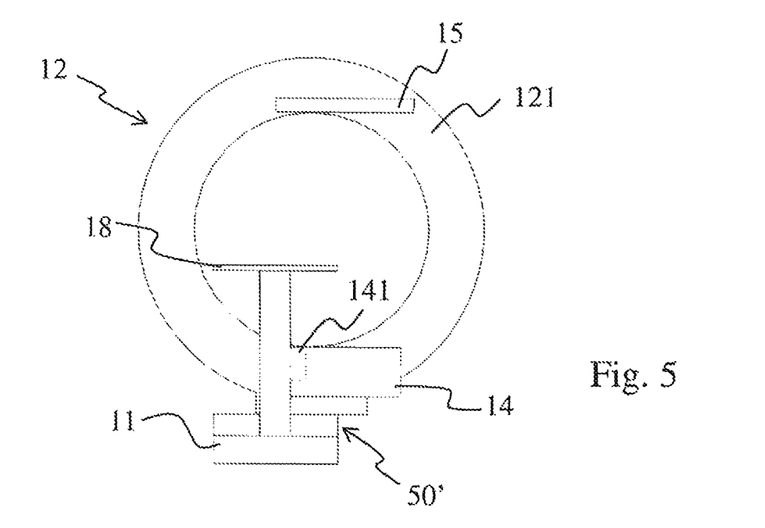
FIG. 5 is a schematic illustration of how elements of the apparatus may be moved to various locations within their defined range of movement.

According to one embodiment, the X-ray source 14 and/or the image detector 15 can further include a housing which is designed and dimensioned to cover the opening 59 through which the mounting bracket 58 extends throughout all positions of the range of lateral movement of the X-ray source 14 and/or image detector 15. With reference to FIG. 5, the effect of such housing is apparent as opening 59 (see FIG. 3) is not visible. Moreover, although the detector 15 can be driven to an extreme position, the detector housing still covers the opening on the surface of the gantry housing 121.

The apparatus can comprise two guiding constructions 50, a first for the X-ray source 14 and a second for the image detector 15. The guiding constructions 50 can comprise the same number of components having the same functions to form similarly functioning assemblies. The first and second guiding constructions may be identical, while optionally the mounting bracket 58 is different as adapted specifically for the X-ray source 14 and the image detector 15.

According to one aspect of the disclosure and referring to FIG. 4, the housing 121 of the support construction 12 for the X-ray imaging components 15, 16 does not encase the imaging assembly components 14, 15 but functions primarily or solely as a housing for e.g. the ring-shaped gantry 122, to which the X-ray imaging apparatus 14, 15 are mounted, and for the structures arranged to the apparatus to drive the X-ray imaging apparatus 14, 15 about the rotation axis 13. This enables the support construction 12 for the X-ray imaging apparatus 14, 15 to be lighter and provides a possibility for better access for patients and personnel to the imaging space between the X-ray imaging components 14, 15. This increased space also clears the line of sight for the apparatus operator into the imaging space volume inside the housing 121 where the patient is positioned for an exposure.

Regarding the aspect of access to the volume between the X-ray imaging apparatus 14, 15, FIG. 5 illustrates how components of the apparatus may be moved to various locations within the ranges of movements available for them. According to that embodiment, laterally moving either or both of the X-ray source 14 and the image detector 15 can be performed to ease patient access to the support construction 12. Another similar construction or some other similarly functioning construction may be arranged in the apparatus to also laterally move the support construction 12 for the X-ray imaging assembly 14, 15 itself, in relation to the elongated frame part 11. By incorporating such linear movement mechanism 50' to the apparatus, e.g. even more room may be provided for the patient to enter the imaging area and then get properly positioned for an exposure.

Thus, according to one aspect of the disclosure, the apparatus further comprises a linear movement mechanism 50' arranged to enable moving the support construction 12 for the X-ray imaging assembly in relation to the longitudinally extending frame part 11 in a direction which is at right angles to the direction in which the longitudinally extending frame part 11 extends, wherein a range of the linear movement of the support construction 12 comprises a base position in relation to the first longitudinally extending frame part 11 and a first and a second extreme position.

Since the support construction 12 for the X-ray imaging assembly components 14, 15 extends in a direction at right angles to the longitudinally extending frame part 11, the direction in which the linear movement mechanism 50' moves the support construction 12 for the X-ray imaging assembly 14, 15 in relation to the longitudinally extending frame part 11 is also at right angles to that direction.

The base position provided by the linear movement mechanism 50' for the support construction 12 for the X-ray imaging assembly 14, 15 as well as that provided by the guiding construction 50 in the various embodiments can be either of the first and second extreme positions and may be the base position.

In the following, various examples are given relating to how to utilize the degrees of freedom of movement of various components of the apparatus the various embodiment of the apparatus provide.

According to one aspect of the disclosure and referring to FIG. 5, a light emitting component 141 is arranged in connection with the X-ray source 14. This light emitting component 141 may be configured to be able to project a light beam of the same shape as is the shape of an X-ray beam the X-ray source 14 is configured to emit or can be adjusted to emit. Such light emitting component 141 may be mounted to the same guiding construction 50 as the X-ray source 14 has, e.g. as a component separate from the X-ray source 14, to be movably mounted in relation to the rest of the components of the apparatus. The range of lateral movement of the guiding construction 50 is then preferably so configured that the X-ray source 14 and the light emitting component 141 can be positioned at the same location within the range of movement the guiding construction 50 provides, which configuration provides a novel arrangement by which one is able to cast a positioning light on the object to be imaged from the very same location at which the actual X-ray imaging exposure is to take place, or begin.

According to another aspect, the control system of the apparatus comprises an input for a patient entry mode, the patient entry mode comprising operating the at least one guiding construction 50 so as to drive at least either of the X-ray source 14 and the image detector 15 to a position closer to the first extreme position than the second extreme position within the range of lateral movement of the X-ray source 14 and/or the image detector 15.

According to one aspect of the disclosure, the apparatus comprises the guiding construction 50 for both the X-ray source 14 and the image detector 15 and the control system of the apparatus comprises an input for a patient entry mode according to which the guiding constructions 50 are driven so as to position both the X-ray source 14 and the image detector 15 closer to the first extreme position than the second extreme position within the ranges of lateral movement of the X-ray source 14 and the image detector 15.

According to another aspect of the disclosure, the apparatus comprises a guiding construction 50 for both the X-ray source 14 and the image detector 15 and the control system of the apparatus comprises an input for a patient entry mode which comprises operating the guiding constructions 50 to move the X-ray source 14 and the image detector 15 in the same direction so as to position them closer to the first extreme position than the second extreme position within the ranges of lateral movement of the X-ray source 14 and the image detector 15.

According to another aspect of the disclosure, the control system of the apparatus comprises an input for a patient entry mode which includes driving the linear movement mechanism 50' so as to position the support construction 12 for the X-ray imaging assembly closer to the first extreme position than the second extreme position within the range of the linear movement of the support construction 12.

According to one aspect of the disclosure, the control system of the apparatus comprises an input for a patient entry mode, the patient entry mode comprising a combination of the two above-described or also other patient entry modes, like to position the X-ray imaging components 14, 15 and their support construction 12 in the same direction or in opposite directions from their base positions.

According to one aspect of the disclosure, the control system of the apparatus comprises an input for a patient entry mode according to which the at least one guiding construction 50 is operated so as to drive at least either of the X-ray source 14 and the image detector 15 to a position closer to the first extreme position than the second extreme position within the range of lateral movement of the X-ray source 14 and/or the image detector 15, and the linear movement mechanism 50' so as to drive the support construction 12 for the X-ray imaging components 14, 15 to a position closer to that of the extreme positions which is closer to the position where the X-ray source 14 and/or the image detector 15 are driven to.

According to one aspect of the disclosure, the patient entry mode comprises the control system controlling the first driving mechanism 16 to move the X-ray imaging components 14, 15 about the rotation axis 13 to drive the X-ray source 14 and the image detector 15 to a rotational position at which the at least one guiding construction 50 is so positioned that the direction of movement enabled by the at least one guiding construction 50 is perpendicular to the direction in which the first longitudinally extending frame part 11 extends.

The above patient entry modes are suitable to be implemented when the construction of the apparatus comprises the X-ray source 14 and the image detector 15 extending outside the gantry housing 121.

Figure 6:
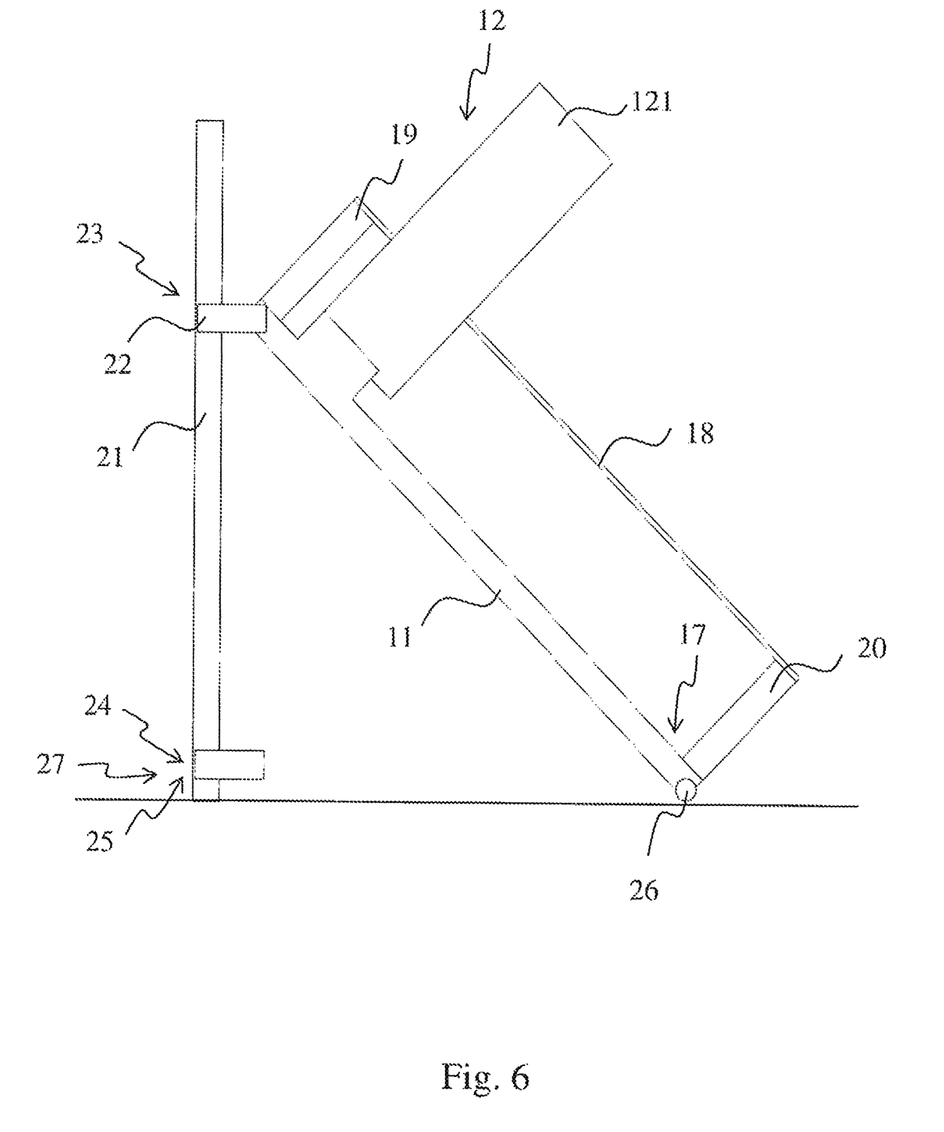
FIG. 6 is a schematic side view of an embodiment like the one shown in FIG. 1 arranged with elements enabling a change in orientation.

Turning to FIG. 6 which shows, as an example and as a schematic general side view, certain components of an embodiment of an apparatus in which, in addition to what can be referred to as a first elongated frame part 11 discussed above, there is a second elongated frame part 21 mechanically connected to the first elongated frame part 11 of essentially the same length as the first elongated frame part 11.

According to one aspect of the disclosure and still referring to FIG. 6, at the proximity of the first end of the elongated frame parts 11, 12 is arranged an articulated connection construction 22 to mechanically connect the first and second elongated frame parts 11, 21, to allow for tilting of the first elongated frame part 11 about at least one tilt axis in relation to the second elongated frame part 21. The at least one tilt axis may be an axis which is orthogonal to the direction in which the first and second elongated frame parts 11, 21 extend as well as to direction in which the support construction 12 for the X-ray imaging assembly 14, 15 extends—perpendicularly from the first longitudinally extending frame part 11.

In the embodiments shown in FIG. 6, the at least one tilt axis is horizontal. This is not to be understood that the tilt axis needs to be horizontal.

According to another aspect of the disclosure, on the side of the second elongated frame part 21, a mounting structure 23 not directly visible in FIG. 6 is arranged in connection with the articulated connection construction 22. The mounting structure 23 is arranged movable along or alongside the second elongated frame part 21.

According to another aspect of the disclosure, in proximity of the second end of the second elongated frame part 21 is arranged a locking mechanism 24 configured to enable connecting and disconnecting the first and second elongated frame parts 11, 21. Particularly, the locking mechanism 24 may be arranged in the proximity of the second end of the first and second elongated frame parts 11, 21 and as configured to enable connecting together and disconnecting the first and second elongated frame parts 11, 21 at the proximity of the second ends of the first and second elongated frame parts 11, 21.

When the second elongated frame part 21 is mounted stable and the locking mechanism 24 is not connecting the first and second elongated frame parts 11, 21, the second end of the first elongated frame part 11 is free to move laterally while the articulated connection 22 between the frame parts 11, 21 allows for turning of the first elongated frame part 11 about the horizontal tilt axis, at the proximity of the first end of the first elongated frame part 11. In case of a vertical starting position, such movably arranged mounting structure as discussed above allows for descending and ascending of the first end of the first elongated frame part 11.

While the construction allowing for tilting of the first elongated frame part 11 and descending and ascending of the first end of the first elongated frame part 11, as well as that of the locking mechanism 24 discussed above may vary, examples of such are disclosed in more detail in a co-pending patent application FI 20190054, which is incorporated herein by reference.

FIG. 6 shows the apparatus according to FIG. 1 at a stage where the first end of the first elongated frame part 11 has moved downwards and the second end of the first elongated frame part 11 has moved horizontally on a surface. The apparatus of FIG. 6 may be configured to allow for descending of the first end of the first elongated frame part 11 all the way to the proximity of the second end of the second elongated frame part 21.

According to yet another aspect of the disclosure, in functional connection with the second elongated frame part 21 is arranged a driving mechanism 27 to drive the mounting structure 23 along or alongside the second elongated frame part 21. When being in mechanical connection with the first elongated frame part 11, at the proximity of the first end of it, the driving mechanism 27 can move the first end of the first elongated frame part 11 in a direction in which the second elongated frame part 21 extends.

The driving mechanism 27 to drive the mounting structure 23 may be a construction similar with the driving mechanism 17 driving the support construction 12 of the x-ray imaging assembly 14, 15 along or alongside the first elongated frame part 11.

According to one aspect of the disclosure, the driving mechanism 27 to drive the mounting structure 23 comprises a chain drive.

To describe some of the features discussed above in other words, in mechanical connection with the articulated connection construction 22, on the side of the second elongated frame part 21, is arranged a mounting structure 23 which is arranged movable along or alongside the second elongated frame part 21, such construction thereby providing a degree of freedom of movement along or alongside the second frame part 21 for the articulated connection construction 23 and for the first end of the first elongated frame part 11 mechanically connected to the articulated connection construction 23.

In an embodiment, the mounting structure 23 is arranged movable along or alongside the second elongated frame part 21 at least essentially a distance corresponding to the length of the first elongated frame part 11, and the articulated connection construction 22 is arranged to allow for tilting of the first elongated frame part 11 between orientations at which the first and second elongated frame parts 11, 21 extend essentially in parallel and at which the first and second elongated frame parts 11, 21 extend essential orthogonally.

According to yet another aspect of the disclosure, the locking mechanism 24 comprises a displacement mechanism 25, which is not directly visible in FIG. 6, to move the second end of the first elongated frame part 11 a distance away from the second elongated frame part 21 when the locking mechanism 24 disconnects the first and second elongated frame parts 11, 21.

According to another aspect of the disclosure, the locking mechanism 24 comprises a motor driven arrangement with mating components on the side of a motorized structure and the first elongated frame part 11, respectively.

The locking mechanism 24 may further comprise a guiding construction configured to guide the second end of the first elongated frame part 11 straight on the locking mechanism 24 when the second end of the first elongated frame part 11 is moving towards the locking mechanism 24. Or, to put it in other words, when the second end of the first elongated frame part 11 moves towards and approaches the second end of the second elongated frame part 21.

According to yet another aspect and as shown as an example in FIG. 6, the first elongated frame part 11 comprises at the proximity of its second end at least one wheel or roller 26.

According to another aspect of the disclosure, instead of the wheel or roller, a structure designed to slide on a surface may be arranged at the second end of the first elongated frame part 11.

Figure 7:
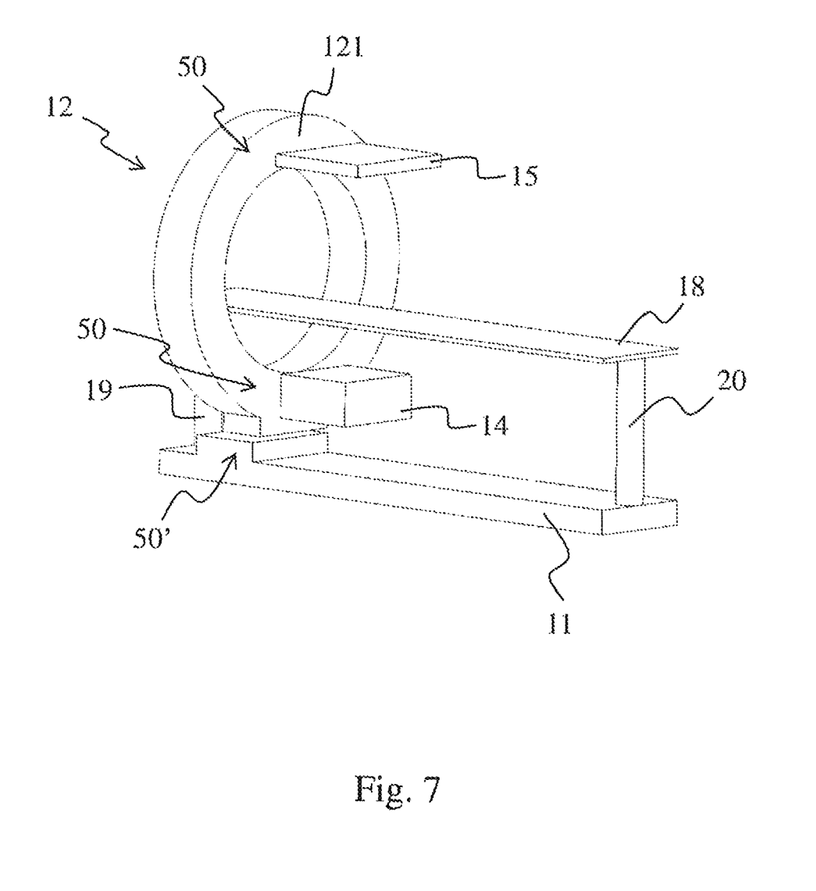
FIG. 7 is a schematic illustration of the apparatus in a horizontal position with certain components driven to locations corresponding to those shown in FIG. 5.

FIG. 7 is a schematic general presentation of an apparatus, as an example, extending in horizontal direction. The apparatus may comprise constructions as discussed in connection with FIG. 6, which allow for changing the direction in which the elongated frame part 11 extends. The support construction 12 for the X-ray imaging assembly 14, 15 in FIG. 7 is not similar with that of FIG. 6, but FIG. 7 rather shows certain components of the apparatus as driven to locations corresponding to those shown in FIG. 5 and discussed above in the context of the patient entry modes.

Figure 8A:
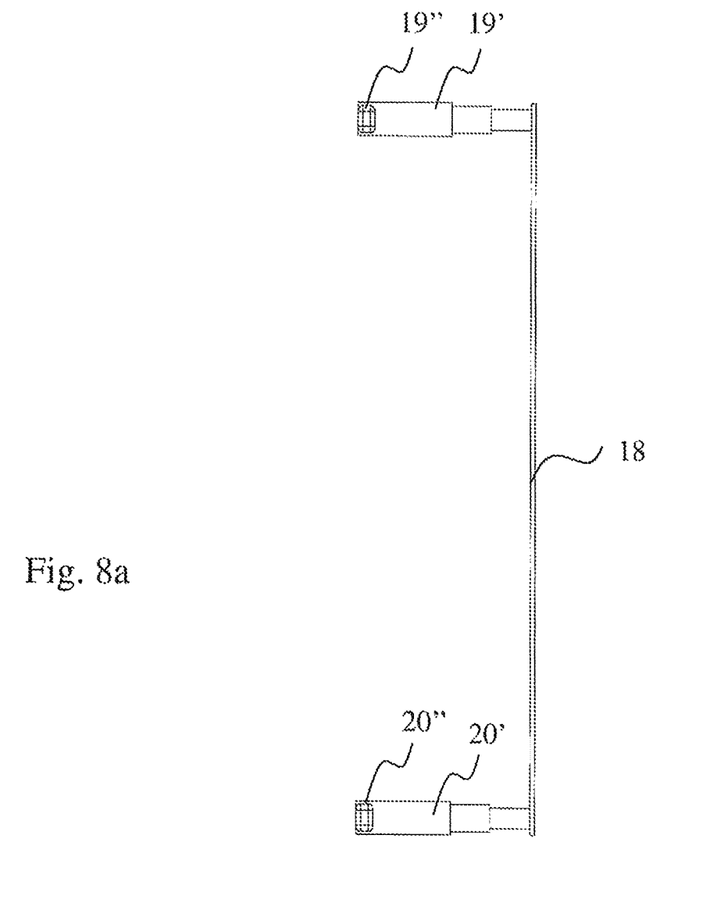
FIG. 8a shows a patient support assembly suitable for use in the imaging apparatus of the present disclosure.

According to yet another aspect and as shown in FIG. 8a, the connection construction 19, 20 which mechanically connects the patient support 18 to the elongated frame part 11 may comprise a patient support adjustment mechanism 19', 20' configured to enable displacing the patient support 18 closer and further away from the (first) elongated frame part 11.

According to another aspect of the disclosure, a patient support driving mechanism 19", 20" is arranged in functional connection with the patient support adjustment mechanism 19', 20'.

According to another aspect of the disclosure, the patient support adjustment mechanism 19', 20' may comprise a first adjustment mechanism 19' arranged together with its driving mechanism 19" comprised in the patient support driving mechanism 19", 20" substantially at the first end of the elongated frame part 11, and a second adjustment mechanism 20' arranged together with its driving mechanism 20" comprised in the patient support driving mechanism 19", 20" substantially at the second end of the elongated frame part 11.

According to one aspect of the disclosure, the patient support adjustment mechanisms 19', 20' is arranged in functional connection with the control system of the apparatus and the control system is configured to control the patient support driving mechanism 19", 20" of the patient support adjustment mechanism 19', 20'.

According to one aspect of the disclosure, the control system is configured to control the connection construction 19, 20 comprising the first adjustment mechanism 19' with its driving mechanism 19", arranged substantially at the first end of the (first) elongated frame part 11, and the second adjustment mechanism 20' with its driving mechanism 20", arranged substantially at the second end of the (first) elongated frame part 11, to keep at the first and second ends of the elongated frame part 11 an identical distance between the (first) elongated frame part 11 and the patient support 18 when adjusting the distance between the two.

According to another aspect of the disclosure, the distance between the ends of the (first) elongated frame part 11 and the patient support 18 can be adjusted to be different.

Figure 8B:
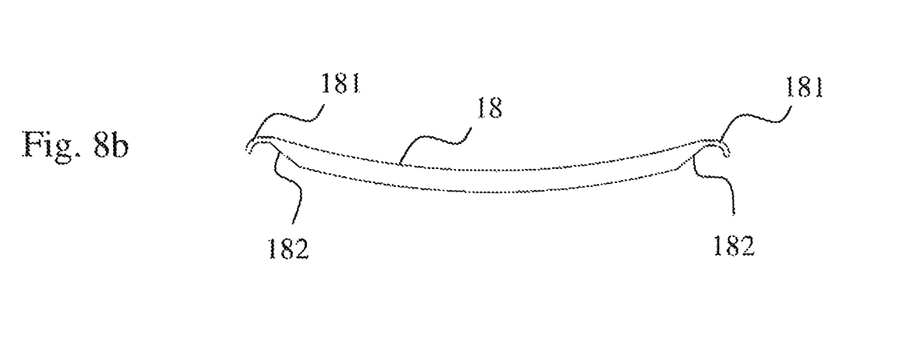
FIG. 8b shows a cross section of an exemplary patient support assembly.

According to one aspect of the disclosure, as shown in FIG. 8b, considering the above-discussed first direction of the patient support 18, its cross section as for its prevailing part is curved to better support a patient against the concave surface of the patient support 18.

According to one other aspect and as shown in FIG. 8b, at the edges 181 of that cross section of the patient support 18, the shape of the cross section turns into being curved in the opposite direction.

According to one other aspect and as further shown in FIG. 8b, near the edges of the above-discussed cross section of the patient support 18 and on the side opposite to the for its prevailing part concave surface, is arranged a holding structure 182. The holding structure 182 may be e.g. an elongated handle or an attachment structure to receive a strap designed to extent on or over the concave side of the patient support 18, to be used to provide further support to the patient and thus to help keeping still during an imaging exposure.

According to one aspect of the disclosure, and as already generally mentioned above, the various degrees of freedoms of movement of the components of apparatus can be taken advantage of when positioning a patient, or to be more exact, an anatomy for an exposure. As an example, considering a situation of a patient's shoulder to be examined while lying on a patient support 18 like the one discussed above, one can first drive the patient support 18 to be located at a height position which is easiest for the patient to get on the patient support 18. Then, when the patient is lying on the patient support 18, at least one of i) the height position of the patient support 18, ii) horizontal position of the support construction 12 for the X-ray imaging assembly 14, 15, and iii) position of at least either of the X-ray source 14 and the image detector 15 within the range of the lateral movement provided therefor can be adjusted so that the desired anatomy will locate at the field of view of the apparatus. This, obviously, within the limits of the degrees of freedoms of movement of the components of the apparatus arranged therefor.

In addition to the structures according to embodiments of the disclosure enabling patient entry and positioning operations as discussed above, they can also be taken advantage of to perform e.g. other than traditional kind CT imaging and, in addition to CT imaging, also imaging modes with no rotation but mere linear movement of the X-ray imaging assembly may be deployed.

Thus, according to one aspect of the disclosure, the apparatus comprises the guiding construction 50 for both the X-ray source 14 and the image detector 15 and the control system of the apparatus comprises an operation mode to drive the motorized construction 53 of the guiding construction 50 to move the X-ray source 14 and the image detector 15, starting from the base positions, a distance in the same direction within said ranges of lateral movement of the X-ray source 14 and the image detector 15, and perform an imaging exposure while rotating the x-ray imaging assembly 14, 15 about an axis.

According to one aspect of the disclosure, the apparatus comprises the guiding construction 50 for both the X-ray source 14 and the image detector 15 and the control system comprises an operating mode to drive the guiding constructions 50 to move the X-ray source 14 and the image detector 15 to a position other than the base position within said ranges of lateral movement of the X-ray source 14 and the image detector 15, and perform an imaging exposure.

According to one aspect of the disclosure, the apparatus comprises the guiding construction 50 for both the X-ray source 14 and the image detector 15 and the control system comprises an operating mode to drive the guiding constructions 50 to move the X-ray source 14 and the image detector 15 to positions which are at an identical distance in the same direction from the base position, within said ranges of lateral movement of the X-ray source 14 and the image detector 15, and perform an imaging exposure.

According to one aspect of the disclosure, an operating mode of the apparatus comprises that prior to the imaging exposure, both the X-ray source 14 and the image detector 15 are driven to locate at the extreme ends in the same direction from their base positions within said ranges of lateral movement of the X-ray source 14 and the image detector 15.

According to one aspect of the disclosure, the apparatus comprises the guiding construction 50 for both the X-ray source 14 and the image detector 15 and the control system comprises an operating mode to drive the guiding constructions 50 to move the X-ray source 14 and the image detector 15 within said ranges of lateral movement of the X-ray source 14 and the image detector 15 during an imaging exposure.

The imaging exposure of the operation modes as of above may comprise the control system controlling driving the first driving mechanism 16 arranged to move the X-ray imaging components 14, 15 about the rotation axis 13.

According to one aspect of the disclosure, the control system comprises at least two imaging modes of the apparatus to operate the first driving mechanism 16 to rotate the X-ray imaging assembly about an axis and simultaneously operate the X-ray imaging assembly components 14, 15 to image an object, out of which in the first imaging mode the X-ray source 14 and the image detector 15 are located at their base positions within the ranges of lateral movement of the X-ray source 14 and the image detector 15 and, in the second imaging mode, both the X-ray source 14 and the image detector 15 have been moved along the guiding construction 50 within the ranges of lateral movement of the X-ray source 14 and the image detector 15 to locate at an identical distance in the same direction from the base positions.

According to one aspect of the disclosure, the apparatus comprises the guiding construction 50 for both the X-ray source 14 and the image detector 15 and the control system comprises an operating mode comprising a first and a second imaging exposure, wherein the first imaging exposure comprises the control system controlling driving the first driving mechanism 16 arranged to move the X-ray imaging assembly components 14, 15 about the rotation axis 13 in a first rotation direction while both the X-ray source 14 and the image detector 15 have been driven to locate at or at the proximity of the first extreme ends in the same direction from the base position within said ranges of lateral movement of the X-ray source 14 and the image detector 15, the second imaging exposure comprises the control system controlling driving the first driving mechanism 16 arranged to move the X-ray imaging assembly components 14, 15 about the rotation axis 13 in a rotation direction opposite to the first rotation direction after both the X-ray source 14 and the image detector 15 have been driven to locate at or at the proximity of the second extreme ends in the same direction from a center position within said ranges of lateral movement of the X-ray source 14 and the image detector 15.

According to one aspect of the disclosure, the control system of the apparatus comprises an imaging mode comprising two imaging scan rotations wherein the first scan comprises moving the X-ray imaging assembly components 14, 15 by the first driving mechanism 16 in a first rotation direction when both the X-ray source 14 and the image detector 15 have been driven, prior to the exposure, in the same direction to locate a distance from their base positions towards the first extreme ends within the ranges of lateral movement of the X-ray source 14 and the image detector 15, and wherein the second scan comprises moving the X-ray imaging assembly components 14, 15 by the first driving mechanism 16 in a second rotation direction opposite to the first direction when both the X-ray source 14 and the image detector 15 have been driven, prior to the exposure, the same distance to locate a distance from said base positions towards the second extreme ends within the ranges of lateral movement of the X-ray source 14 and the image detector 15.

According to one aspect of the disclosure, the operation modes like described above optionally comprises rotation in said first and second directions over an angle more than 180 degrees yet less than 360 degrees.

Figure 9:
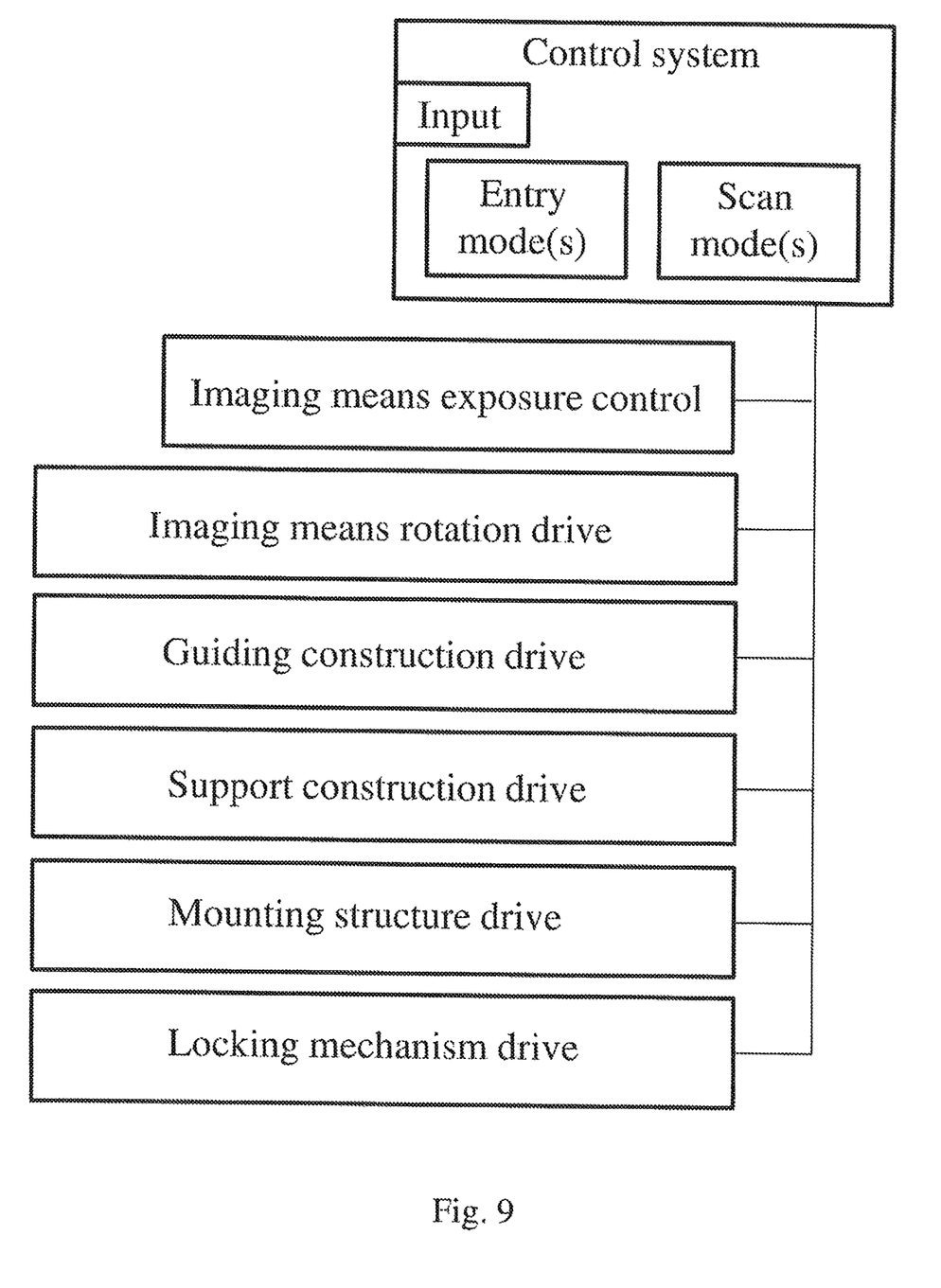
FIG. 9 is a block diagram showing an example of a control system of the apparatus.

FIG. 9 shows as a block diagram an example of components of a control system. The control system according to FIG. 9 is configured to enable controlling, first of all, operation of the X-ray source 14 and the image detector 15 during an exposure. Components controlling operation of the X-ray source 14 and the image detector 15 can include components physically arranged to the X-ray source 14 and/or the image detector 15 and/or elsewhere in the apparatus.

The control system of FIG. 9 further controls various driving of the apparatus elements, such as those rotating the X-ray imaging assembly 14, 15 supported by their support construction 20, those driving the one or more guiding construction 50 as well those moving the support construction 20 for the imaging assembly 14, 15 itself. FIG. 9 further shows the control system comprising at least one patient entry mode which includes controlling at least one of the above-mentioned driving elements. Correspondingly, the at least one scanning mode is included in the control system of FIG. 9.

Further shown in FIG. 9 is a signal path to the mounting structure 23 as discussed further above and, in case of the apparatus comprising a motorized locking mechanism 24 to connect and disconnect the first and second elongated frame parts 11, 21 as discussed above, the control system may also control driving of the locking mechanism 24.

Overall, the control system may be arranged to control all the above-discussed operations or any portion thereof. The structures and functionalities discussed above offer various possibilities to ease positioning and perform imaging of a patient.

To aid the Patent Office and any readers of this application and any resulting patent in interpreting the claims appended hereto, applicants do not intend any of the appended claims or claim elements to invoke 35 U.S.C. 112(f) unless the words "means for" or "step for" are explicitly used in the particular claim.

The exemplary embodiment(s) has been described with reference to the preferred embodiments. Obviously, modifications and alterations will occur to others upon reading and understanding the preceeding description. It is intended that the exemplary embodiment(s) be construed as including all such modifications and alterations insofar as they come within the scope of the appended claims or equivalents thereof.

The invention claimed is:

1. A dental or medical CT imaging apparatus, comprising:
   a first longitudinally extending frame part extending in a first direction and comprising a first end and a second end;
   a support construction extending from the longitudinally extending frame part in a second direction at least substantially perpendicular to the first direction, the support construction comprising a ring-shaped gantry connected to the first longitudinally extending frame part as non-rotatable about an axis extending in said second direction;
   an X-ray source and an image detector which together form an X-ray imaging assembly mounted to the support construction;
   a first driving mechanism arranged to move the X-ray imaging assembly about a virtual or physical rotation axis extending in parallel with said first direction;
   a control system comprising an operation mode controlling the first driving mechanism and simultaneously the X-ray imaging assembly;
   a patient support and a connection construction mechanically connecting the patient support to the first longitudinally extending frame part;
   wherein the support construction includes at least one guiding construction configured to enable laterally moving at least either of the X-ray source and the image detector in relation to the support construction, said laterally moving comprising moving on a plane extending at right angles to said virtual or physical rotation axis, a range of said lateral movement of at least either of the X-ray source and the image detector comprising a base position and a first and a second extreme position, and wherein each of the first and the second extreme position is laterally disposed relative to the base position.

2. The apparatus according to claim 1, wherein the lateral movement of the X-ray source and/or the image detector is at least substantially perpendicular to the rotation axis.

3. The apparatus according to claim 1, wherein the at least one guiding construction comprises a carriage mounted to the X-ray source and/or the image detector to enable laterally moving the X-ray source and/or the image detector.

4. The apparatus according to claim 3, wherein the guiding construction comprises at least one guiding groove or rail on a side of the support construction and a mating construction on a side of the carriage.

5. The apparatus according to claim 1, wherein the guiding construction includes a position sensor arrangement configured to acquire information relating to a position of the X-ray source and/or the image detector within said range of lateral movement.

6. The apparatus according to claim 1, wherein a signal path is provided between the at least one guiding construction and the control system.

7. The apparatus according to claim 6, wherein the signal path comprises a signal path between the position sensor arrangement and the control system.

8. The apparatus according to claim 1, further comprising a mounting bracket fixed to the carriage and the X-ray source and/or the image detector, to mechanically connect the X-ray source and/or the image detector to the guiding construction.

9. The apparatus according to claim 1, further comprising a light emitting component configured to project a light beam of an at least substantially similar shape as the X-ray source is configured to emit an X-ray beam, and wherein the operation range of the guiding construction is configured to enable positioning the light beam and the X-ray beam at the same position in relation to the support construction.

10. The apparatus according to claim 1, wherein the apparatus includes a second driving mechanism configured to move the support construction in a direction substantially parallel with the first direction.

11. The apparatus according to claim 1, wherein the control system includes a patient entry mode according to which the at least one guiding construction is operated so as to drive at least one of the X-ray source and the image detector to a position relatively closer to the first extreme position than the second extreme position.

12. The apparatus according to claim 1, wherein the apparatus comprises a linear movement mechanism arranged to move the support construction in a direction which is at least substantially perpendicular to the first direction and wherein a range of said linear movement of the support construction comprises a base position in relation to the first longitudinally extending frame part and a first and a second extreme position.

13. The apparatus according to claim 12, wherein the control system of the apparatus includes a patient entry mode which includes driving the linear movement mechanism so as to position the support construction closer to the first extreme position than the second extreme position within the range of the linear movement of the support construction.

14. The apparatus according to claim 13, wherein the control system includes a patient entry mode according to which the at least one guiding construction is operated so as to drive at least one of the X-ray source and the image detector to a position closer to the first extreme position than the second extreme position within the range of lateral movement of the X-ray source and/or the image detector, and the linear movement mechanism is operated to drive the support construction to a position closer to one of the first and second extreme position within the range of the linear movement of the support construction which is closer to the position where the X-ray source and/or the image detector is driven.

15. The apparatus according to claim 11, wherein the patient entry mode comprises the control system controlling the first driving mechanism to move the X-ray imaging assembly about the rotation axis to a rotational position at which the at least one guiding construction is positioned such that a direction of movement enabled by the at least one guiding construction is at least substantially perpendicular to the first direction of the first longitudinally extending frame.

16. The apparatus according to claim 1, wherein the patient support includes a surface which extends substantially parallel to the first longitudinally extending frame part.

17. A dental or medical CT imaging apparatus, comprising:
    a first longitudinally extending frame part extending in a first direction and comprising a first end and a second end;
    a support construction extending from the longitudinally extending frame part in a second direction at least substantially perpendicular to the first direction;
    an X-ray source and an image detector which together form an X-ray imaging assembly mounted to the support construction;
    a first driving mechanism arranged to move the X-ray imaging assembly about a virtual or physical rotation axis;
    a control system, wherein the control system comprises at least one operation mode of the apparatus to operate the first driving mechanism and simultaneously operate the X-ray imaging assembly;
    wherein the support construction includes at least one guiding construction configured to enable laterally moving at least either of the X-ray source and the image detector in relation to the support construction, said laterally moving comprising moving on a plane extending at right angles to said virtual or physical rotation axis, a range of said lateral movement of at least either of the X-ray source and the image detector comprising a base position and a first and a second extreme position, and wherein each of the first and the second extreme position is laterally disposed relative to the base position;
    wherein the apparatus further comprises a connection construction mechanically connecting a patient support to the first longitudinally extending frame part, said connection construction extending perpendicular to the longitudinally extending frame part, and a patient support adjustment mechanism configured to enable movement of the patient support closer and away from the first longitudinally extending frame part while in connection with the first longitudinally extending frame part.

18. The apparatus according to claim 17, said connection construction including a driving mechanism to drive a mounting structure along a second longitudinally extending frame part wherein the driving mechanism is in mechanical connection in a proximity of a first end of the first longitudinally extending frame part, and wherein the driving mechanism can move the first end of the first longitudinally extending frame part in a direction in which the second longitudinally extending frame part extends.

19. The apparatus according to claim 18, including a locking mechanism comprising a guiding construction configured to guide the second end of the first longitudinally extending frame part straight on the locking mechanism when the second end of the first longitudinally extending frame part is moving towards the locking mechanism, and wherein the first longitudinally extending frame part comprises at the proximity of its second end at least one wheel or roller or a structure designed to slide on a surface.

20. A dental or medical CT imaging apparatus, comprising:
    a first longitudinally extending frame part extending in a first direction and comprising a first end and a second end;
    a support construction extending from the longitudinally extending frame part in a second direction at least substantially perpendicular to the first direction;
    an X-ray source and an image detector which together form an X-ray imaging assembly mounted to the support construction;
    a first driving mechanism arranged to move the X-ray imaging assembly about a virtual or physical rotation axis;
    a control system, wherein the control system comprises at least one operation mode of the apparatus to operate the first driving mechanism and simultaneously operate the X-ray imaging assembly;
    wherein the support construction includes at least one guiding construction configured to enable laterally moving at least either of the X-ray source and the image detector in relation to the support construction, said laterally moving comprising moving on a plane extending at right angles to said virtual or physical rotation axis, a range of said lateral movement of at least either of the X-ray source and the image detector comprising a base position and a first and a second extreme position, and wherein each of the first and the second extreme position is laterally disposed relative to the base position;
wherein the apparatus further comprises a connection construction mechanically connecting a patient support to the first longitudinally extending frame part and a patient support adjustment mechanism configured to enable movement of the patient support closer and away from the first longitudinally extending frame part while in connection with the first longitudinally extending frame part,
wherein a mounting structure is arranged movable along a second longitudinally extending frame part and an articulated connection construction is arranged to allow for tilting of the first longitudinally extending frame part.

* * * * *